US008007789B2

(12) United States Patent
Selva et al.

(10) Patent No.: US 8,007,789 B2
(45) Date of Patent: Aug. 30, 2011

(54) ANTIBIOTICS GE 81112 FACTORS A, B, B1, PHARMACEUTICALLY ACCEPTABLE SALTS AND COMPOSITIONS, AND USE THEREOF

(75) Inventors: Enrico Selva, Gropello Cairoli (IT); Flavia Marinelli, Milan (IT); Daniele Losi, Rovellasca (IT); Linda Cavaletti, Rovellasca (IT); Ameriga Lazzarini, Legnano (IT); Alessandra Marazzi, Saronno (IT)

(73) Assignee: Vicuron Pharmaceuticals Inc., King of Prussia, PA (US)

( * ) Notice: Subject to any disclaimer, the term of this patent is extended or adjusted under 35 U.S.C. 154(b) by 355 days.

(21) Appl. No.: 12/147,215

(22) Filed: Jun. 26, 2008

(65) Prior Publication Data

US 2009/0023665 A1 Jan. 22, 2009

Related U.S. Application Data

(62) Division of application No. 10/496,009, filed as application No. PCT/EP02/11113 on Oct. 4, 2002, now Pat. No. 7,407,654.

(30) Foreign Application Priority Data

Nov. 28, 2001 (EP) .................................. 01128204

(51) Int. Cl.
*A61K 35/00* (2006.01)

(52) U.S. Cl. ........................................................ 424/115
(58) Field of Classification Search .................. None
See application file for complete search history.

(56) References Cited

U.S. PATENT DOCUMENTS

| 5,432,193 A | 7/1995 | Carter et al. |
| 5,484,717 A | 1/1996 | Zaccardi |
| 7,407,654 B2 * | 8/2008 | Selva et al. .................. 424/115 |

FOREIGN PATENT DOCUMENTS

| EP | 0 422 818 | 4/1991 |
| WO | 94/14838 | 7/1994 |
| WO | 96/08460 | 3/1996 |

OTHER PUBLICATIONS

Watve et al., "How many antibiotics are produced by the genus *Streptomyces*?", Arch. Microbiol., 176:386-390, 2001.

* cited by examiner

*Primary Examiner* — Elli Peselev
(74) *Attorney, Agent, or Firm* — Brandon Boss; Michael J. Moran; E. Victor Donahue

(57) ABSTRACT

The invention relates to antibiotic substances of microbial origin, arbitrarily denominated antibiotic GE 811112 factor A, factor B1 and factor B, which are produced by fermentation of *Streptomyces* sp. DSMZ 14386, the pharmaceutically acceptable salts and composition thereof, and their use as an antibacterial agent having activity versus susceptible microbes.

2 Claims, 11 Drawing Sheets

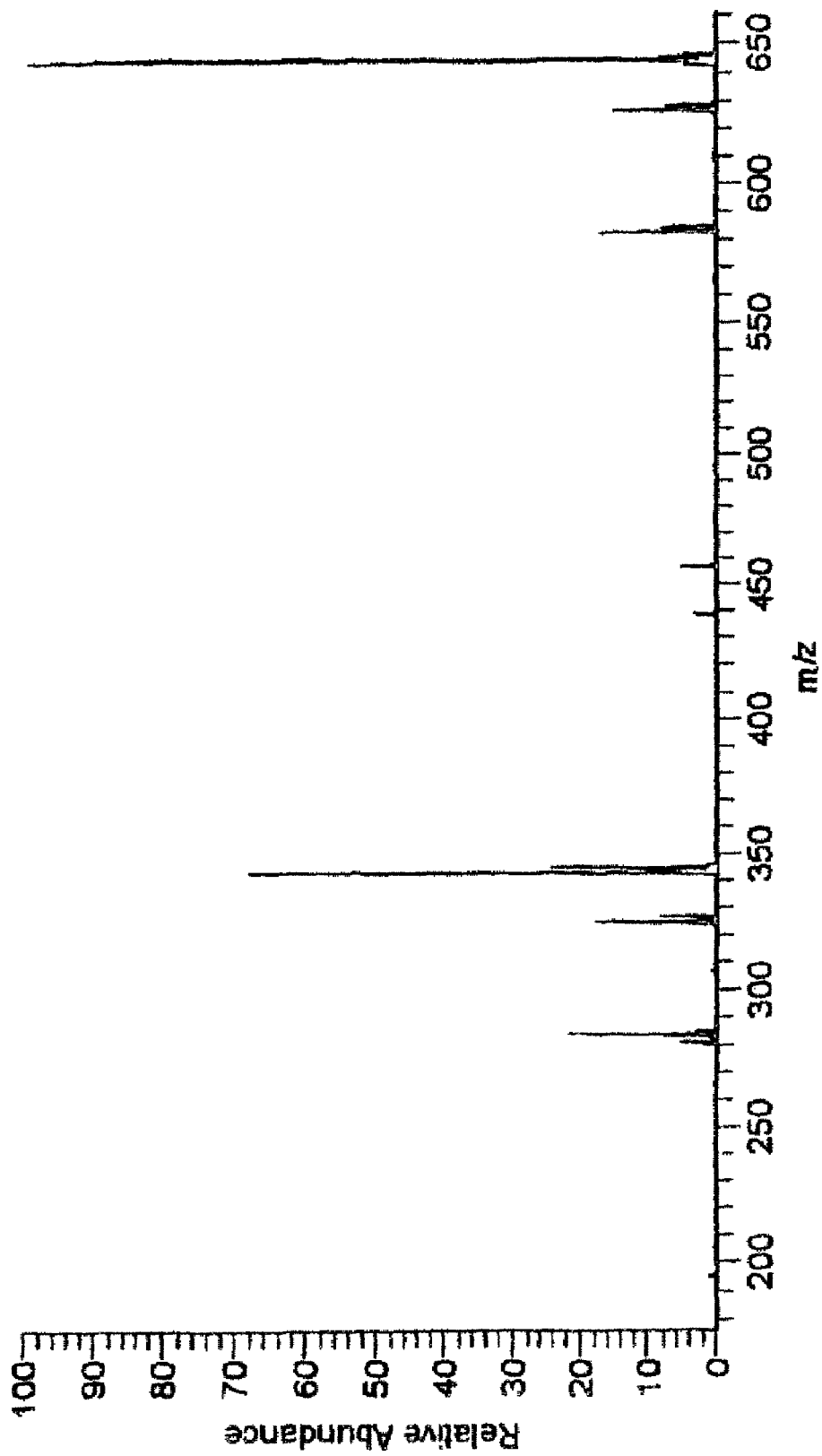
Figure 1: MsMs spectrum of GE 81112 factor A after fragmentation of the monoprotonated ion at m/z = 644 with a normalized collisions energy of 25%.

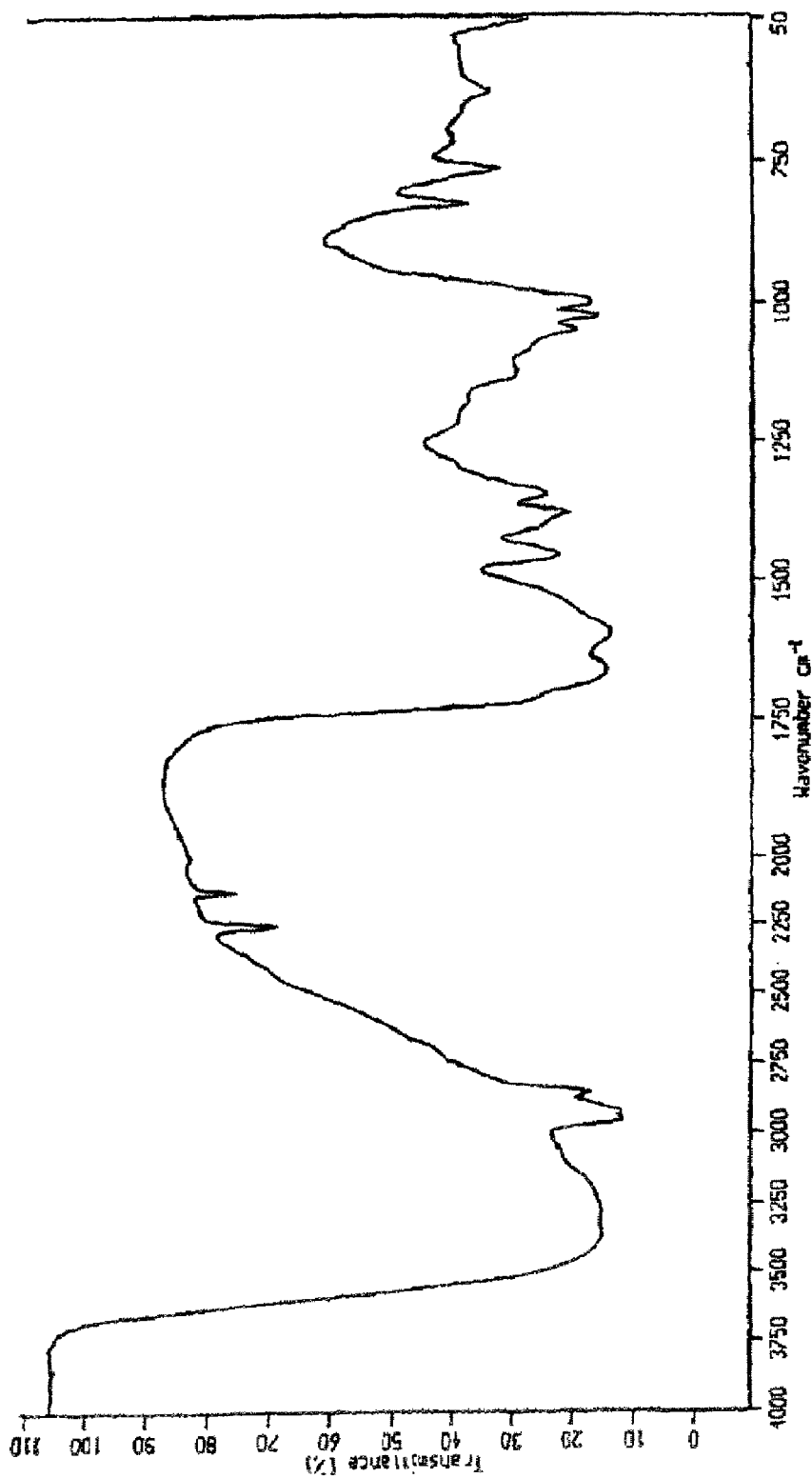
Figure 2: Infrared spectrum of GE 81112 factor A in nujol

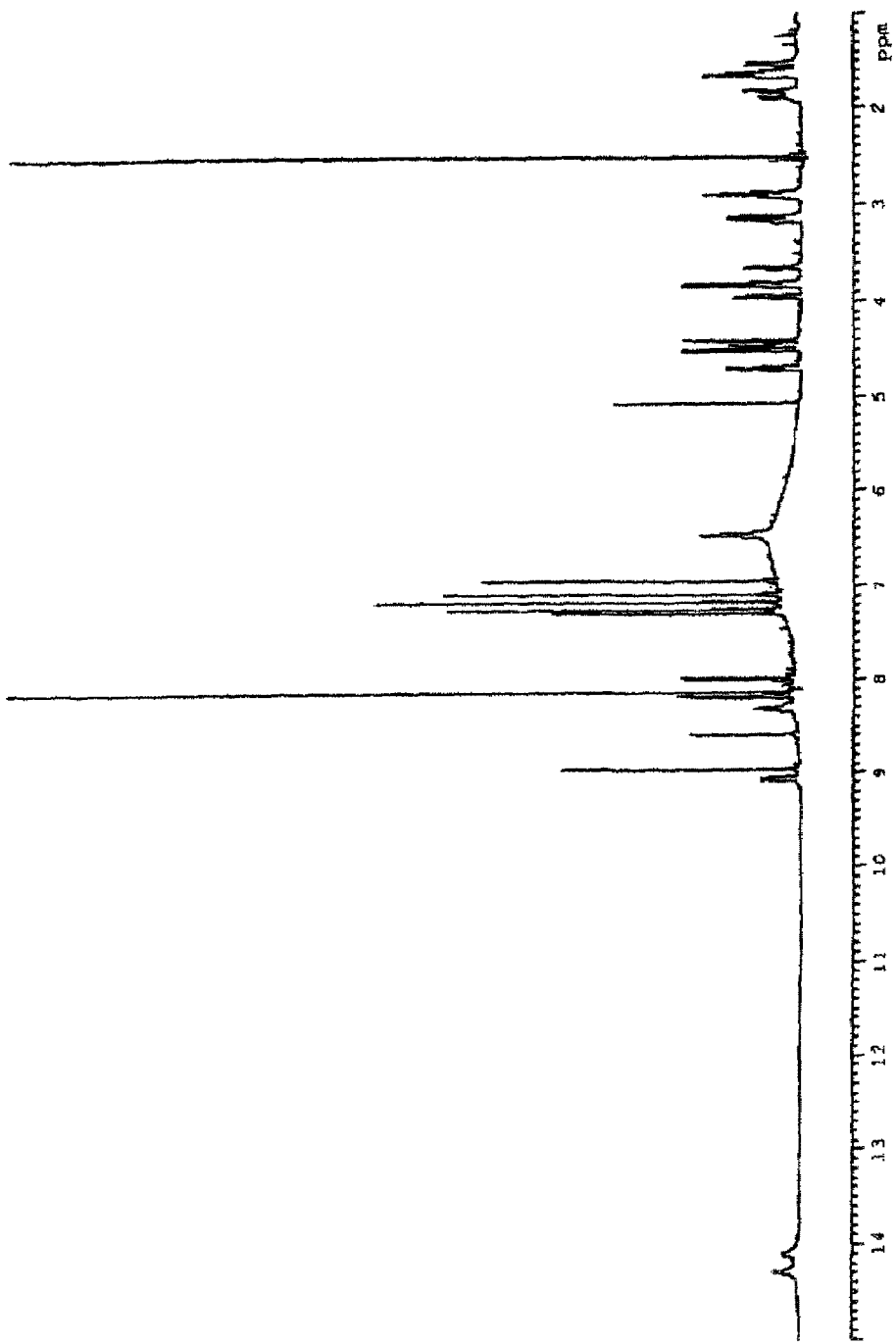
Figure 3: $^1H$ spectrum of GE 81112 factor A in DMSO-$d_6$ and TFA (drops)

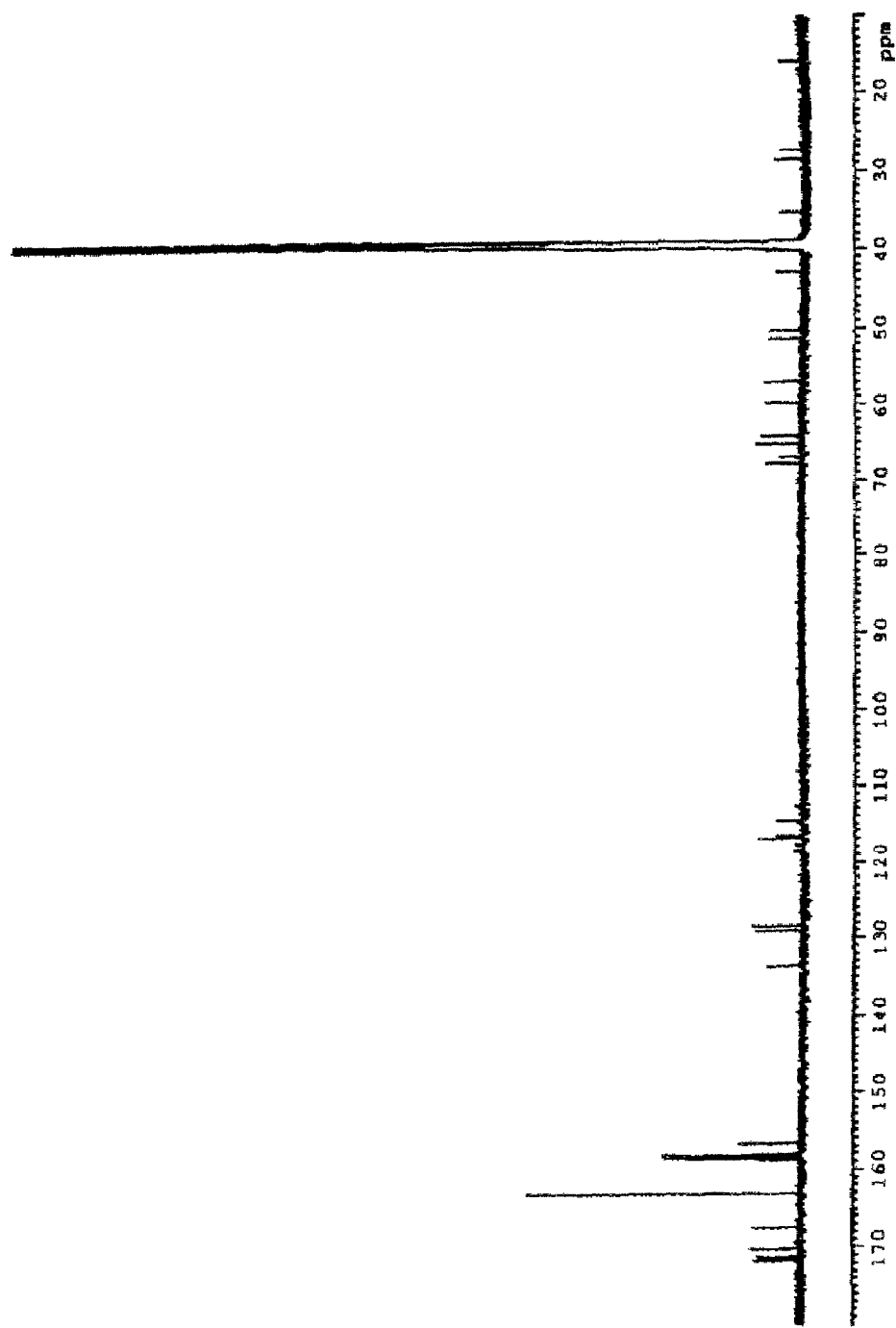
Figure 4: $^{13}C$ spectrum of GE 81112 factor A in DSMO-$d_6$ and TFA (drops)

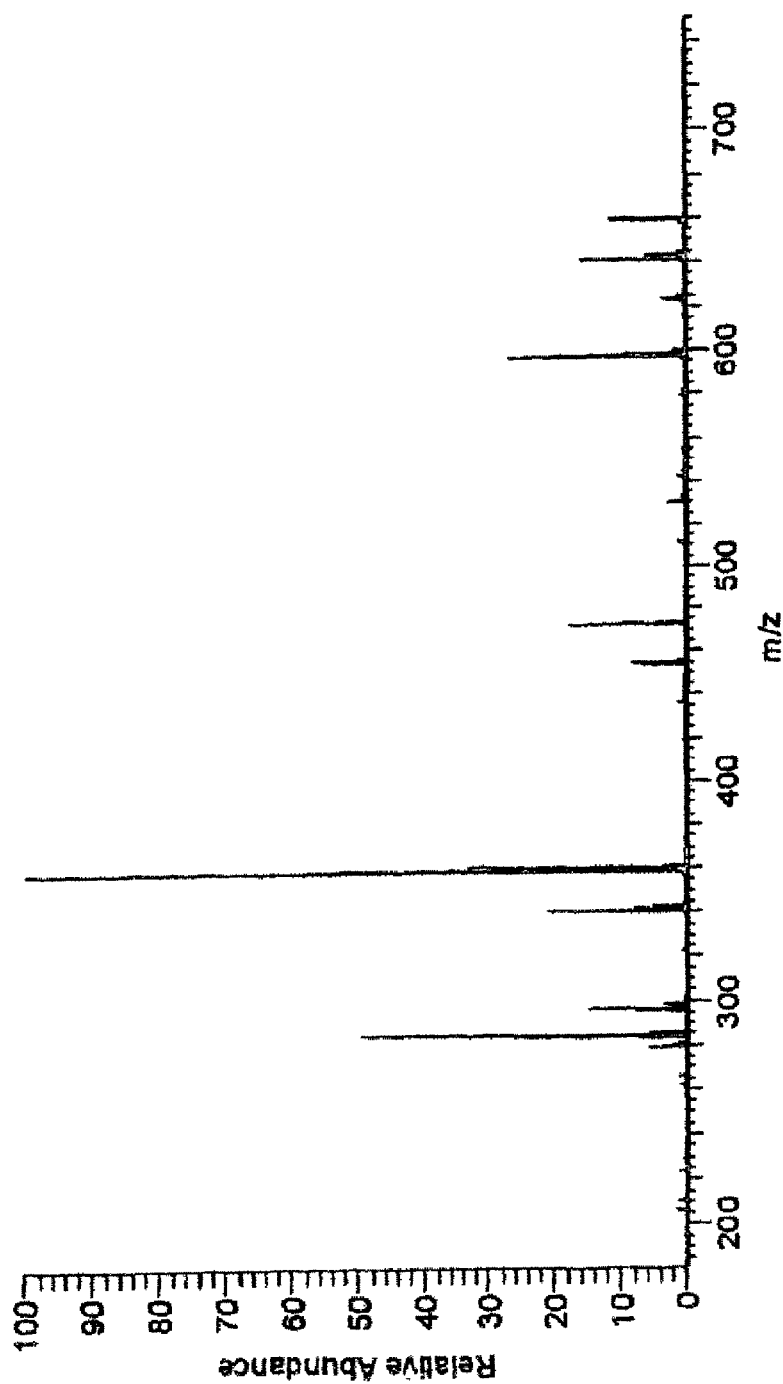
Figure 5: MsMs spectrum of GE 81112 factor B after fragmentation of the monoprotonated ion at m/z = 659 with a normalized collisions energy of 28%.

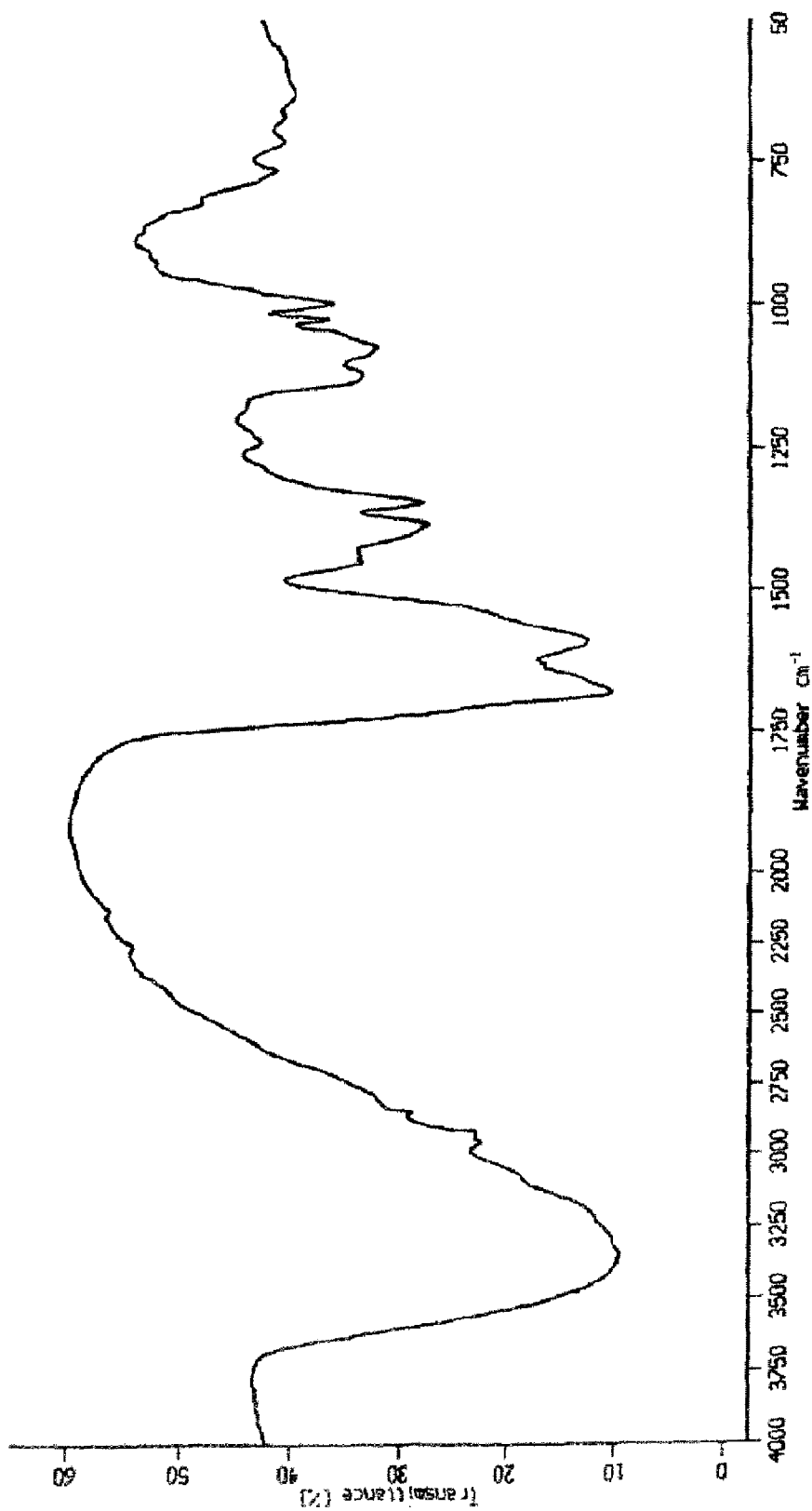
Figure 6: Infrared spectrum of GE 81112 factor B in KBr

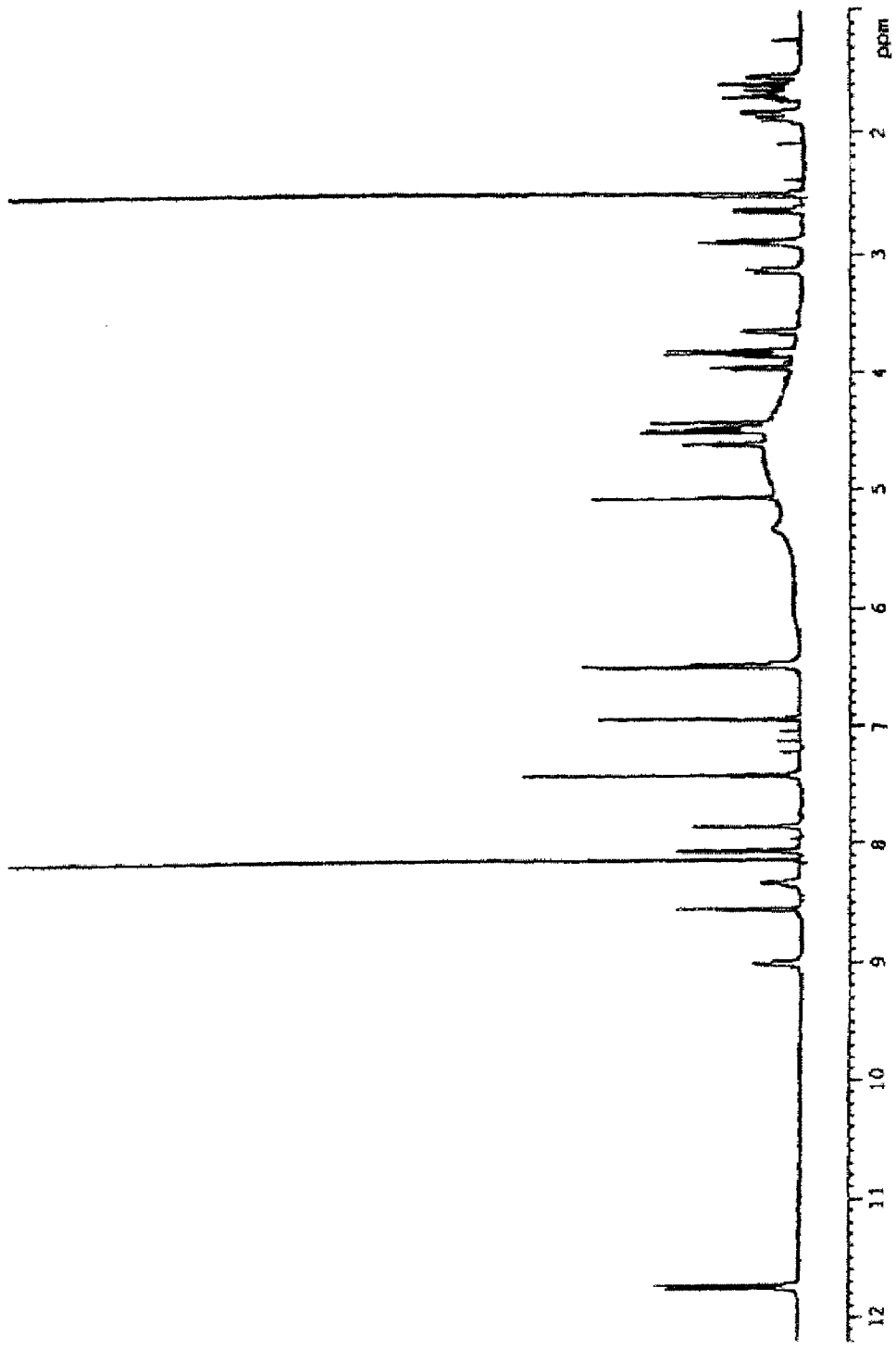

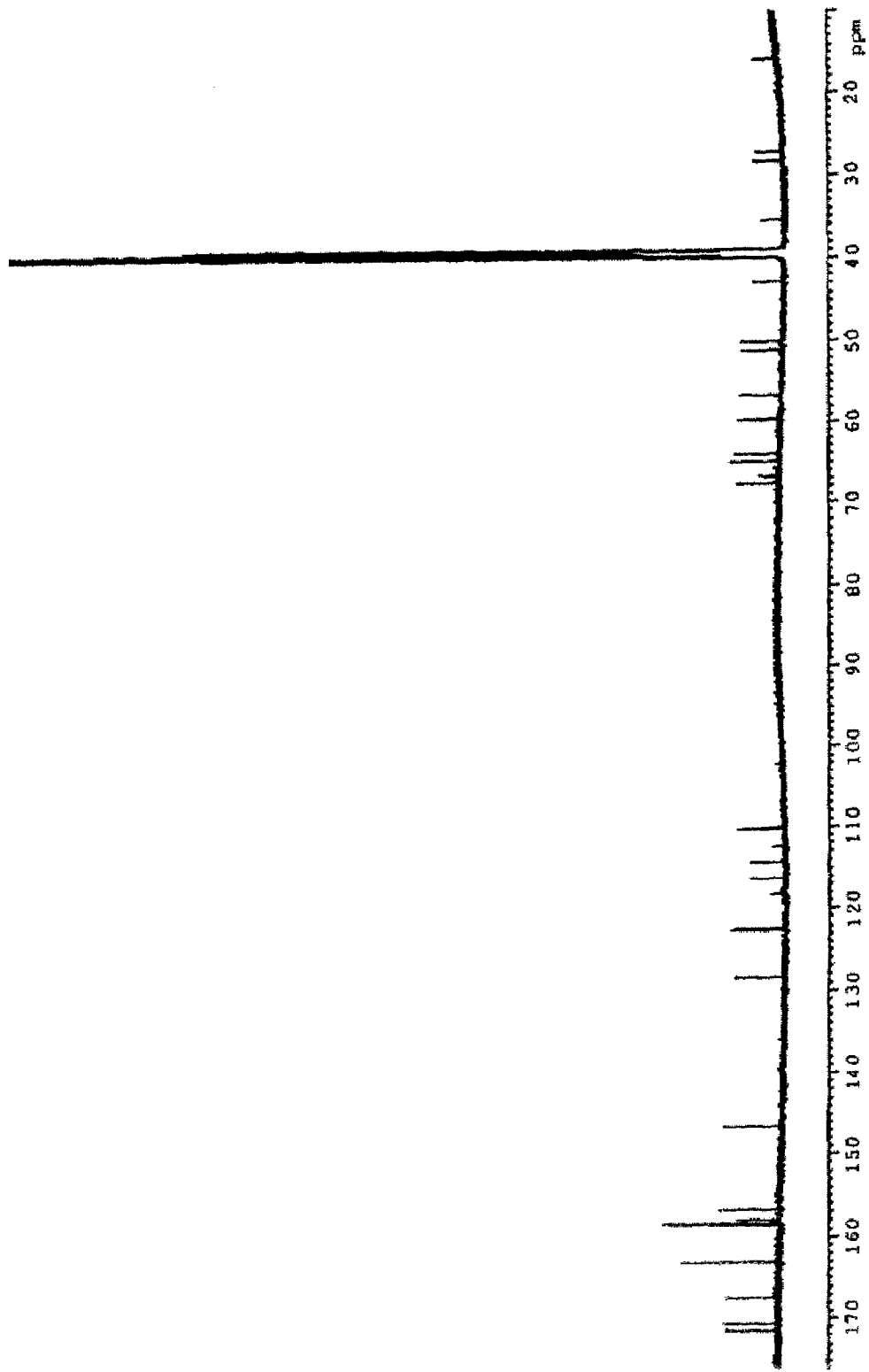
Figure 8: $^{13}C$ spectrum of GE 81112 factor B in DSMO-d$_6$ and TFA (drops)

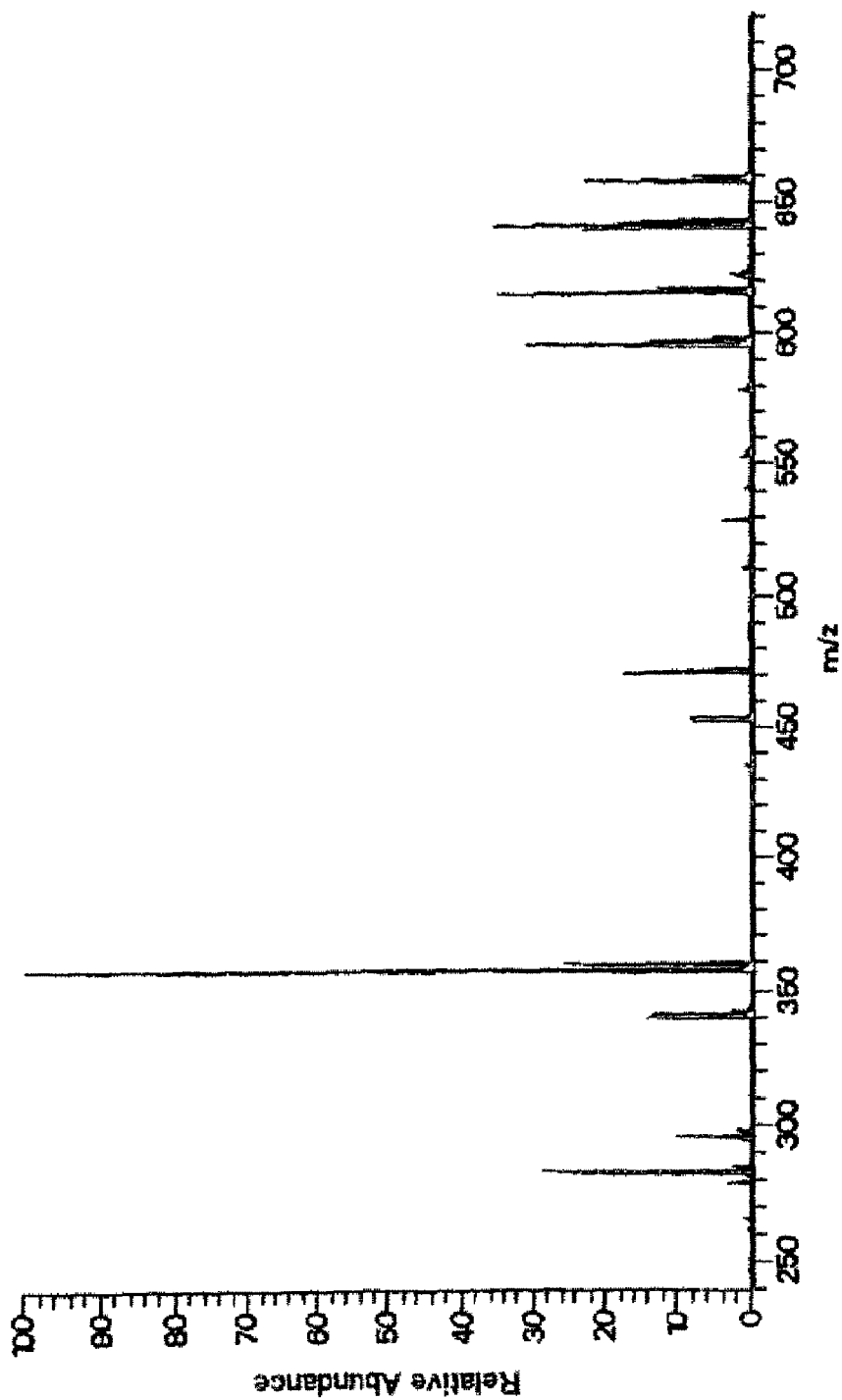
Figure 9 : MsMs spectrum of GE 81112 factor B1, after fragmentation of the monoprotonated ion at m/z = 658 with a normalized collisions energy of 25%.

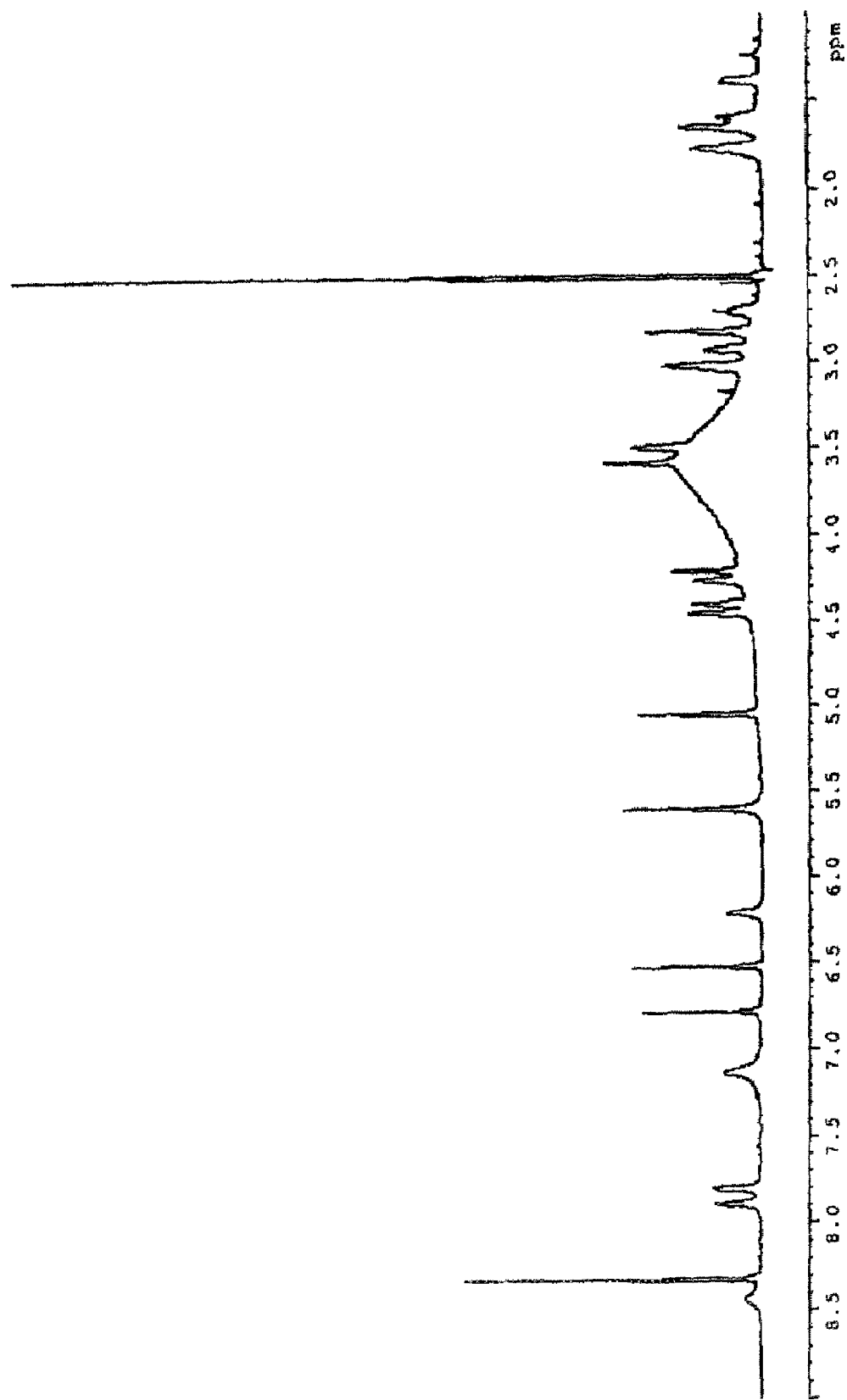

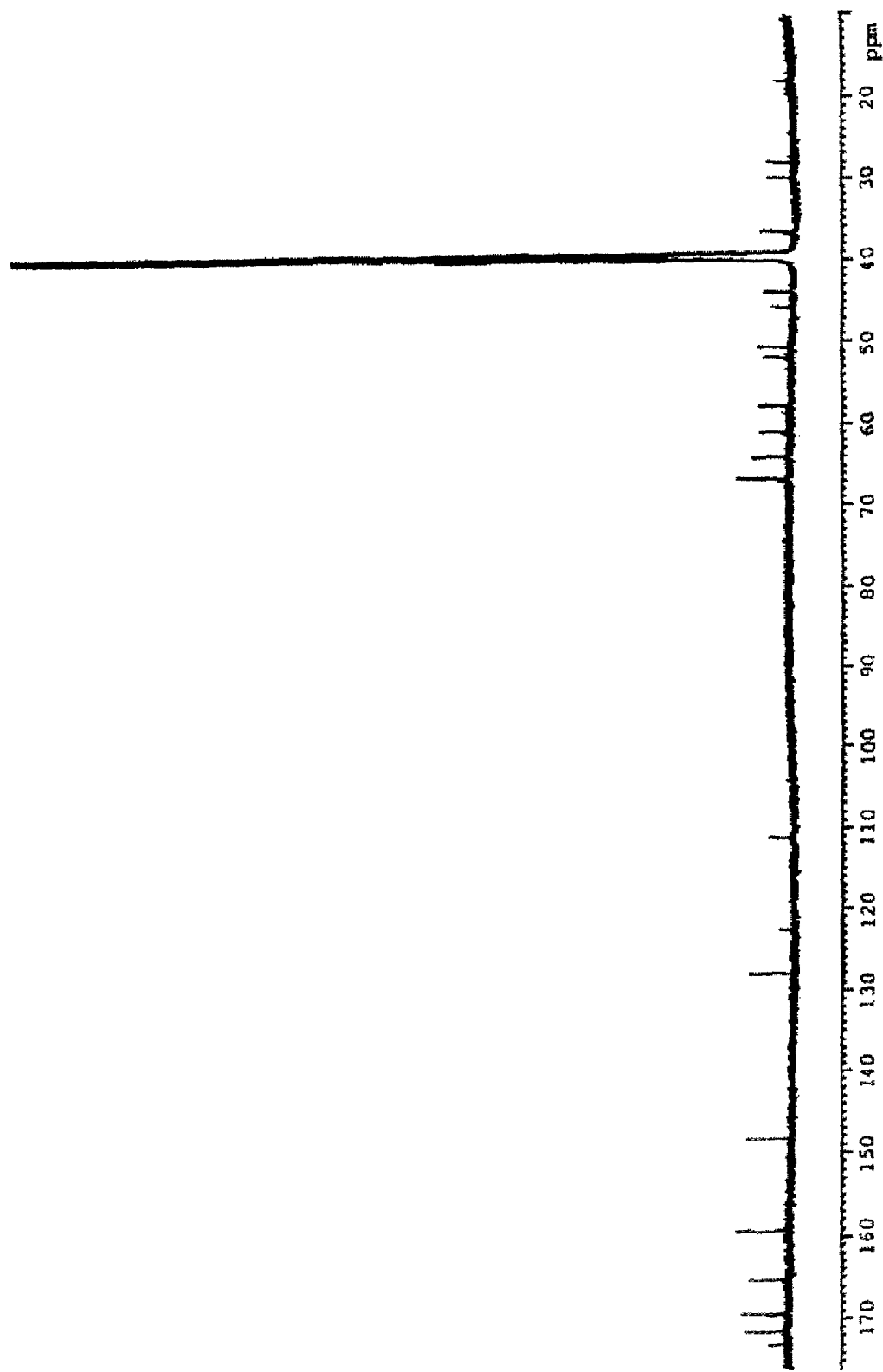
Figure 11: $^{13}C$ spectrum of GE 81112 factor B1 in DMSO-$d_6$

US 8,007,789 B2

ANTIBIOTICS GE 81112 FACTORS A, B, B1, PHARMACEUTICALLY ACCEPTABLE SALTS AND COMPOSITIONS, AND USE THEREOF

The present application is a division of U.S. application Ser. No. 10/496,009, filed Sep. 21, 2004, now U.S. Pat. No. 7,407,654, which represents the U.S. national stage of PCT/EP02/11113, as internationally filed on Oct. 4, 2002, and which claims priority of EP 01128204.3, filed Nov. 28, 2001.

The present invention concerns an antibiotic substance of microbial origin, arbitrarily denominated GE 81112 factor A, GE 81112 factor B and GE 81112 factor B1, a mixture of said factors in any proportion, the pharmaceutically acceptable salts and compositions thereof, and their use as an antibacterial agent.

Another object of the present invention is a process for preparing GE 81112 factor A, GE 81112 factor B and GE 81112 factor B1, a mixture of said factors in any proportion, hereinafter reported as GE 81112 compounds or GE 81112 antibiotics.

BRIEF DESCRIPTION OF THE DRAWINGS

FIG. 1 provides the MsMs spectrum of GE 81112 factor A after fragmentation of the monoprotonated ion at m/z=644 with normalized collisions energy of 25%

FIG. 2 provides the infrared spectrum of GE 81112 factor A in nujol.

FIG. 3 provides $^1$H spectrum of GE 81112 factor A in DMSO-$d_6$ and TFA (drops).

FIG. 4 provides the $^{13}$C spectrum of GE 81112 factor A in DMSO-$d_6$ and TFA.

FIG. 5 provides the MsMs spectrum of GE 81112 factor B after fragmentation of monoprotonated ion at m/z=659 with a normalized collisions energy of 28%.

FIG. 6 provides the infrared spectrum of GE 81112 factor B in KBr.

FIG. 7 provides the $^1$H spectrum of GE 81112 factor B in DMSO-$d_6$ and TFA (drops).

FIG. 8 provides the $^{13}$C spectrum of GE 81112 factor B in DMSO-$d_6$ and TFA (drops).

FIG. 9 provides the MsMs spectrum of GE 81112 factor B1, after fragmentation of the monoprotonated ion at m/z=658 with a normalized collisions energy of 25%.

FIG. 10 provides the $^1$H spectrum of GE 81112 factor B1 in DMSO-$d_6$.

FIG. 11 provides the $^{13}$C spectrum of GE 81112 factor in DMSO-$d_6$.

STRAIN AND FERMENTATION

*Streptomyces* sp. DSMZ 14386 originally designed with the internal code GE 81112 was isolated from a soil sample and deposited on Jul. 16, 2001, with the DSMZ, (Deutsche Sammlung von Mikroorganismen und Zellkulturen GmbH, Mascheroder Weg 1b, D-38124 Braunschweig, Germany), under the provision of the Budapest Treaty. The strain was accorded accession number DSMZ 14386.

The production of GE 81112 compounds is achieved by cultivating a *Streptomyces* strain capable of producing them, i.e. *Streptomyces* sp. DSMZ 14386 or a variant or mutant thereof maintaining the genetic ability to produce said GE 81112 compounds; isolating the resulting antibiotic from the culture broth; purifying the isolated antibiotic; and separating the antibiotic three factors A, B and B1 or their mixture by chromatographic means. In any case, it is preferred to produce compounds GE 81112 under aerobic conditions in an aqueous nutrient medium containing assimilable sources of carbon, nitrogen, and inorganic salts, purifying the resulting compounds by means of chromatographic techniques. Many of the nutrient media usually employed in the fermentation field can be used, however certain media are preferred.

Preferred carbon sources are glucose, xilose, starch, fructose, glycerol, and the like. Preferred nitrogen sources are soybean meal, peptone, meat extract, yeast extract, tryptone, aminoacids, hydrolized casein and the like. Among the inorganic salts which can be incorporated in the culture media, there are the customary soluble salts capable of yielding sodium, potassium, iron, zinc, cobalt, magnesium, calcium, ammonium, chloride, carbonate, sulphate, phosphate, nitrate, and the like ions.

Preferably, the strain producing the GE 81112 compounds is pre-cultured in a fermentation tube or in a shake flask, then the culture is used to inoculate jar fermentors for the production of substantial quantities of substances. The medium used for the pre-culture can be the same as that employed for larger fermentations, but other media can also be employed. The strain producing the GE 81112 compounds can be grown at temperature between 20° C. and 40° C., preferably between 22° C. and 37° C. No growth it is observed at temperature higher than 44° C.

During the fermentation, the GE 81112 factors can be monitored by bioassay on susceptible microorganisms and/or by HPLC analyses. Maximum production of GE 81112 compounds generally occurs after circa 20 hours and before the 80 hours of fermentation.

Compounds GE 81112 are produced by cultivating *Streptomyces* sp. DSMZ 14386 or a variant or mutant thereof producing compounds GE 81112, and are found in the culture broths.

Morphological Characteristics of *Streptomyces* sp. DSMZ 14386

*Streptomyces* sp. DSMZ 14386 grows well on many standard solid media. Microscopic examination and cell dimensions were measured using the culture grown on one-tenth strength humic acid medium (H. Nonomura, 1984—Design of a new medium for isolation of soil actinomycetes. The Actinomycetes 18, 206-209).

In liquid culture (V6 medium, see Example 1 for composition), no fragmentation of the mycelium was observed after 2 days of growth at 28° C.

Microscopic examination on HV/2 agar after 15 days of incubation at 28° C. revealed a not fragmented nor extensively branched vegetative mycelium. Aerial mycelium was not extensively branched too. Aerial hyphae generating chains of more than 10 (mostly >20) spores; these were arranged in simple, not very compact spirals of 3 to 5 loops. Spore shapes ranged from globose (average diameter about 0.9 μm) to ovoid or cylindrical (0.8 to 0.9 by 1.1 to 1.3 μm).

Cultural Characteristics of *Streptomyces* sp. DSMZ 14386

*Streptomyces* sp. DSMZ 14386 was grown for two days in V6 liquid medium (see Example 1 for medium composition). The mycelium was harvested by centrifugation and washed three times with sterile saline solution and then diluted to provide a suitable inoculum. Aliquots of the suspension were streaked in a cross-hatched manner onto various media recommended by Shirling and Gottlieb (E. B. Shirling and D. Gottlieb, 1966—Method for Characterization of *Streptomyces* species—Int. J. Syst. Bacteriol., 16, 313-340) and several media recommended by Waksman (Waksman S. A., 1961—The Actinomycetes—The Williams and Wilkins Co., Baltimore. Vol 2, pp 328-334).

The ability to use a variety of carbohydrates as a carbon and energy source was determined in ISP8 medium (Shirling and Gottlieb, ibid) containing the carbon source at a final concentration of 1% (w/v). NaCl tolerance as well as ability to grow at different temperatures was determined onto ISP2 medium. All media were incubated at 28° C. for 21 days; descriptions are referred to 14 days unless specified. Colour was assessed in natural daylight, using the Colour Atlas of Maerz and Paul (A. Maerz and M. R. Paul, 1950—A Dictionary of Colour, 2nd edition. McGraw-Hill Book Co. Inc., New York). Ability to reduce nitrates to nitrites was evaluated in Nitrate Broth (ISP8 medium) after overnight incubation at 28° C. in aerobic condition using Bacto-Nitrite Test Strips (Difco), following the protocol suggested by the manufacturer.

Growth, colonial appearance, substrate and aerial mycelium colour and pigment production for strain *Streptomyces* sp. DSMZ 14386 are recorded in Table I. Growth was present on all media used except for G1 agar, which is the only one having inorganic nitrogen source. No characteristic pigmentation was shown on any medium used. Physiological characteristics of the strain are presented in Table II. *Streptomyces* sp. DSMZ 14386 showed the ability to grow up to 7% (w/v) NaCl; at concentration of 1% (w/v) NaCl and higher the strain did not differentiate aerial mycelium. Gelatine liquefaction and milk peptonization were weakly detectable after 7 days of growth. The ability to utilise various carbohydrates for growth is shown in Table III. On the basal medium without any carbon source addition, scant growth of vegetative and aerial mycelium was observed. White aerial mycelium was produced on all carbon sources used except for Glucose.

TABLE I growth characteristics of *Streptomyces* sp. DSMZ 14386

| MEDIUM | GROWTH & MORPHOLOGY | REVERSE COLOUR CODE |
|---|---|---|
| ISP 2 Yeast extract-Malt extract agar | Abundant growth, convolute, becoming crusty nearly the ends of streaks; orange/brown; discolored at growing margins. Tufts of white aerial mycelium. No soluble pigments produced. Deep smell of soil. | 12 L 9 |
| ISP 3 Oatmeal agar | Abundant growth with smooth surface; cream-yellowish. Thin layer of white aerial mycelium only close to the growing margins. No soluble pigments produced. | 11 H 3 |
| ISP 4 Inorganic salts-Starch agar | Abundant growth, convolute, becoming crusty nearly the ends of streaks; yellowish. Presence of white aerial mycelium, cottony. No soluble pigments produced. Deep smell of soil. | 10 F 3 |
| ISP 5 Glycerol-Aspargine agar | Discrete to good growth; colorless to light yellow; feathered and discolored margins. Presence of thin, white aerial mycelium, turning to pinkish (10A2) with aging. No soluble pigments produced. | 10 G 2 |
| ISP 6 Peptone-yeast extract-iron agar | Discrete growth, wrinkled nearly the ends of streaks; colonies small in diameter; little spread from area of streaks; glutinous; light brown. No aerial mycelium produced. Slight darkening of the medium. | 11 J 3 |
| ISP 7 Tyrosine agar | Abundant growth, convolute, becoming crusty nearly the ends of streaks; brown; feathered and discolored margins. Good production of white aerial mycelium, powdery. Brown soluble pigment produced. Slight smell of soil. | 14 L 9 |
| SYE Starch-yeast extract agar | Abundant growth, convolute, becoming crusty nearly the ends of streaks; yellow/brown; wide, feathered and discolored margins. Scant production of white, thin aerial mycelium. No soluble pigments produced. Slight smell of soil. | 10 L 7 |
| CZ-GLU Czapeck-glucose agar | Discrete to good growth, crusty nearly the ends of streaks; colonies small in diameter; cream-light brown; feathered margins. Scant production of white, thin aerial mycelium. No soluble pigments produced. Slight smell of soil. | 12 H 6 |
| GAUZE 1 agar | Absence of growth. | — |
| GAUZE 2 agar | Good growth, thinly wrinkled and crusty nearly the ends of streaks, flat at intersections among streaks; yellowish/brown. Scant presence of thin, white aerial mycelium in the flat areas. Slight darkening of the medium. | 11 L 6 |
| NA Nutrient agar | Discrete to good growth, smooth; cream/yellowish. No aerial mycelium produced. No soluble pigments produced. | 11 L 2 |
| SE Soil extract agar | Barely visible vegetative mycelium; colorless; little spread from area of streaks. No aerial mycelium produced. No soluble pigments produced. | ND |
| HV/2 Humic acid-vitamins agar | Good growth of vegetative mycelium, deeply penetrating into the agar; dark brown; feathered margins. Presence of white aerial mycelium, powdery. | ND |

TABLE II physiological characteristics of *Streptomyces* sp. DSMZ 14386

| TEST | REACTION |
|---|---|
| Starch hydrolysis | Positive |
| Casein hydrolysis | Negative |
| Calcium malate digestion | Positive |
| Litmus milk peptonization | Positive (weak) |
| Litmus milk coagulation | Negative |
| Gelatin liquefaction | Positive (weak) |
| Tyrosine reaction | Positive |
| $H_2S$ production (4 days): | Negative |
| on ISP6 + lead acetate strips | Weakly positive |
| Nitrate reduction | Negative |
| NaCl tolerance | ≦7% |

TABLE III utilization of carbon sources by *Streptomyces* sp. DSMZ 14386

| Carbon source | Vegetative Mycelium Growth | Aerial Mycelium Growth |
|---|---|---|
| Arabinose | + | +/− |
| Fructose | ++ | ++ |
| Inositol | + | +/− |
| Mannitol | ++ | + |
| Raffinose | ++ | ++ |
| Rhamnose | ++ | ++ |
| Sucrose | − | +/− |
| Xylose | ++ | ++ |
| Glucose | ++ | − |

++ good growth; + moderate growth; − scant/no growth;

Chemotaxonomical Characteristics OF *Streptomyces* sp. DSMZ 14386

*Streptomyces* sp. DSMZ 14386 was grown in Sauton's medium for four weeks and then the mycelium was harvested, washed three times with sterile distilled water and subsequently freeze-dried. The stereoisomeric form of the diaminopimelic acid (DAP) was determined according to the method of Staneck and Roberts, (J. L. Staneck and G. D. Roberts, Simplified approach to identification of aerobic actinomycetes by thin-layer chromatography, Appl. Microbiol. 28, 226-231, 1974).

For the extraction of fatty acids, the wet biomass was extracted using minor modifications (L. D. Kuykendall, M. A. Roy, J. J. O'Neill and T. E. Devine, Fatty acid, antibiotic resistance, and deoxyribonucleic acid homology groups of *Bradyrhizobium japonicum*, Int. J. System. Bact. 38, 351-361, 1988) of the method of Miller (L. T. Miller, A single derivatization method for bacterial fatty acid methyl esters including hydroxy acids, J. Clin. Microbiol. 16, 584-586, 1982). Analysis were carried out as described by R. M. Kroppenstedt (R. M. Kroppenstedt, E. Stackebrandt and M. Goodfellow, Taxonomic revision of the actinomycete genera *Actinomadura* and *Microtetraspora*, System. Appl. Microbiol. 13, 148-160, 1990) and data examined using the Microbial Identification System (L. T. Miller, ibid).

The strain *Streptomyces* Sp. DSMZ 14386 contains LL-diaminopimelic acid in the peptidoglycan. Mycolic acids are absent. Iso- and anteiso-branched type fatty acids are present whereas no hydroxy fatty acids or 10-methyl-branched fatty acids are detectable, i.e. fatty acid type 2c *Streptomyces* type.

Identity of Strain *Streptomyces* Sp DSMZ 14386

The strain producing compounds GE 81112 is assigned to the genus *Streptomyces* because of the following morphological and chemical characteristics:
- the formation of a branched not fragmented vegetative mycelium. Aerial hyphae generating chains of more than 10 (mostly >20) arthrospores;
- the presence of LL-diaminopimelic acid in the cell wall and the fatty acid profile of 2c type according to Kroppenstedt (R. M. Kroppenstedt, Fatty acid and menaquinone analysis of actinomycetes and related organisms, pp. 173-199, in: Chemical Methods in bacterial Systematics, M. Goodfellow and D. E. Minnikin eds; London, Accademic Press, 1985).

As with other microorganisms, the characteristics of the strain producing the GE 81112 compounds are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Streptomyces* sp. DSMZ 14386 which maintain the genetic ability to produce GE 81112 compounds are deemed equivalent to it for the purpose of this invention and therefore within the scope of invention.

The antibiotic may be recovered from the supernatant fraction of the fermented broth.

Extraction and Purification of GE 81112 Compounds

The recovery of GE 81112 compounds from the fermentation broths of the producing microorganism is conducted according to known per se techniques such as extraction with solvents, in the presence of adjuvants, precipitation by adding non-solvents, salts, or by changing the pH of the solution, partition chromatography, reverse-phase partition chromatography, ion-exchange chromatography, molecular exclusion chromatography and the like.

A procedure for recovering the antibiotic substance of the invention from the fermentation broth includes extraction of GE 81112 mixture by ion exchange chromatography. According to this procedure, the filtered fermentation broth can be contacted with an ion exchange resin. The elution can be conducted by a variation of pH or ionic-strength. Examples of ion exchange resins that can be conveniently used in the recovery of the compounds of the invention, are both anionic and cationic ion exchange resins, i.e. resins consisting of a matrix of, for instance, synthetic polymers (e.g. polystyrene, acrylic polymers) or natural polymers (e.g. cellulose, sepharose polymers, silica) which are derivatized by introducing an acid (e.g. COOH, $-SO_3H$) or basic (e.g., $-N(CH_3)_2$, $-N^+(CH_3)_3$) functions.

Examples of the above resins are: Dowex 50W resin (Dow Chemical Co.), Amberlite IR-200 and IR-120 (Rohm & Haas), PL-SCX-1000 and APL-SCX 4000 A (Polymer Laboratories), Isolute SCX IST (international sorbent technology), SP Sepharose fast flow and SP Sephadex G25 (Pharmacia Biotech).

An alternative procedure for recovering the antibiotic substances includes adsorption on a proper matrix followed by elution with a polar water miscible solvent or a mixture thereof, concentration to water residue under reduced pressure, and precipitation with a precipitating agent of the type already mentioned above. The pH can be adjusting at an appropriate value. Examples of adsorption matrixes that can be conveniently used in the recovery of the compounds of the invention, are activated charcoal (e.g. Darco G60, Norit CG1), polystyrene or mixed polystyrene-divinylbenzene resins (e.g. Diaion HP 20, Mitsubishi Chemicals, M112 or S112, Dow Chemical Co.; Amberlite XAD2 or XAD4, Rohm & Haas) acrylic resins (e.g. XAD7 or XADB, Rohm & Haas), phenolic adsorbents (e.g. Duolite XAD761, Rohm & Haas), polyamide resins such as polycaprolactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., west Germany; PA 400, M. Woelm A G, West Germany PVP-CL, Aldrich Chemie GmbH & Co., KG, West Germany), controlled pore cross-linked dextrans (e.g. Sephadex LH-20, Pharmacia Fine Chemicals, AB). Charcoal and/or polystyrene resins are commonly employed, particularly preferred being the resin Diaion HP 20, (Mitsubishi Chemicals).

The absorption on an adsorption matrix of the type mentioned above can be employed also as a procedure for purifying the crude product recovered from the fermentation broth, for instance, by means of ion (e.g. cation) exchange chromatography.

The preferred solvent for eluting the GE 81112 compounds from the adsorption matrix depends on the specific stationary phase. In the case of charcoal the elution is achieved by changing to an acid pH the eluting buffer, which typically contains a water miscible solvent, e.g., a lower ketone such as acetone or a lower alcohol such as methanol. Accordingly, the aqueous mixture is adjusted to the appropriate pH value. In the case of polystyrene resins, polystyrene-divinylbenzene resins, acrylic resins or polyamide resin a preferred eluent is a water miscible solvent or its aqueous mixtures, e.g. a mixture of water and a ($C_1$-$C_3$) alkanol.

The term "water-miscible solvent" as used in this application, when not otherwise specified, is intended to have the meaning currently given to it in the art and refers to solvents that, at the conditions of use, are miscible with water in a reasonably wide concentration range, suitable for the intended use. Examples of water-miscible organic solvents that can be used in the elution of the compounds of the invention are: lower alkanols, e.g. ($C_1$-$C_3$) alkanols such as methanol, ethanol, and propanol; phenyl ($C_1$-$C_3$) alkanols such as benzyl alcohol; lower ketones, e.g. ($C_3$-$C_4$) ketones such as acetone and ethyl methyl ketone; cyclic ethers such as dioxane and tetrahydrofuran; glycols and their products of partial etherification such as ethylene glycol, propylene glycol, and ethylene glycol monomethyl ether, lower amides such as dimethylformamide and diethylformamide; acetic acid, dimethylsulfoxide and acetonitrile.

An alternative method for recovering GE 81112 compounds from the fermentation broth is the extraction of GE 81112 compounds or their salts, with water-immiscible organic solvents, by adjusting the pH at an appropriate value, and/or by salting and/or by adding a proper organic salt forming a ion pair with the antibiotic which is soluble in the extraction solvent. The antibiotic may then be precipitated from the concentrated extracts, for example by adding a precipitating agent.

The term "water-immiscible solvent" as used in this application, is intended to have the meaning currently given in the art and refers to solvents that, at the conditions of use, are slightly miscible or practically immiscible with water. Examples of water-immiscible organic solvents that can be used in the extraction of the compounds of the invention from the fermentation broth are: alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopenthyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol, and 3-decanol; ketones of at least five carbon atoms such as methylisopropylketone, methylisobutylketone, methyl-n-amylketone, methylisoamylketone and mixtures thereof.

Examples of convenient ion pairs with the GE 81112 compounds are obtained by addition of acids, such as sulfonic acids represented by p-toluensulfonic, pentan-, esan-, eptansulfonic acids and the like or carboxylic acids rapresented by esanoic, eptanoic, benzoic acids and the like, at the proper pH. Alternatively, ion pairs can be generated by adding cations such as triethylammonium, tetrabutylammonium and the like, at the proper pH.

Purification of the crude GE 81112 compounds, can be accomplished by any of the known per se techniques but is preferably conducted by means of chromatographic procedures. Conveniently, also the so called steric exclusion chromatography technique can be employed with good results. In particular, controlled pore cross-linked dextrans wherein most hydroxyl groups are alkylated, e.g. Sephadex LH-20 (Pharmacia Fine Chemicals, AB), are usefully employed in this technique.

For instance, medium pressure liquid chromatographic separation systems may be employed, using reverse phase chromatography on RP-8 or RP-18 functionalised silica gel and eluting with an ammonium formate solution. The crude product isolated from the fermentation broth, as well as the purified product, usually contains a mixture of the single GE 81112 factors A, B1 and B in variable proportion, depending on both the fermentation and purification conditions.

The separation and purification of individual factors A, B and B1 may be conveniently carried out by semipreparative HPLC of a preparation containing a mixture of GE 81112 compounds.

A preferred preparative HPLC technique for the isolation of pure GE 81112 factors A, B1 and B is performed on a semipreparative HPLC instrument (Shimadzu-LC8A) equipped with a Hibar Lichrosorb (Merck) 25×250 mm column RP8 (7 µm particle size) which is eluted in at 35 ml/min flow rate with 40 mM ammonium formate brought to pH 4.5 with formic acid. The eluates of repeated chromatographic runs containing the separated GE 81112 factors are pooled according to their content and are concentrated under reduced pressure to aqueous solutions, which are freeze dried yielding purified GE 81112 factors A, B1 and B.

As usual in this field, the production as well as the recovery and the purification steps may be monitored by a variety of analytical procedures including bioassay with susceptible microorganisms and/or HPLC procedures. A preferred analytical HPLC technique is performed on a Shimadzu LC10 instrument equipped with a 250×4.6 mm column packed with Symmetry (Waters) or Altima (Alltech) 5 µm particle size C18 stationary phase, eluted at 1 ml/min flow rate with 40 mM ammonium formate brought to pH 4.5 with formic acid. Detection was at 230 nm. In these conditions, Factor A, B1 and B typically showed 13, 18, 21 min retention times, respectively.

Since the antibiotic substances of the invention possess acid and basic functions they can exist also in the form of internal salts or zwitterions at appropriate pH values. Moreover, they can form salts according to conventional procedures. Representative and suitable acid addition salts of the compounds of the invention include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of the bases which can form addition salts with the GE 81112 compounds are: alkali metal or alkaline-earth metal hydroxides such as sodium, potassium, and calcium, hydroxide; ammonia and organic aliphatic, alicyclic or aromatic amines such as methylamine, dimethylamine, trimethylamine, and picoline.

The transformation of a free or zwitterionic compound of the invention into the corresponding salt, and the reverse, i.e. the transformation of a salt of a compound of the invention into the zwitterionic or free compound form, are within the ordinary technical skill and are encompassed by the present invention.

For instance, a compound of the invention can be transformed into the corresponding acid or base addition salt by dissolving the non-addition salt form in an aqueous solvent and adding a slight molar excess of the selected acid or base. The resulting solution or suspension is then lyophilized to recover the desired salt.

In case the final salt form is unsoluble in a solvent where the non-salt form is soluble, it is recovered by filtration from the solution.

The non-salt form can be prepared from a corresponding acid or base salt dissolved in an aqueous solvent which is then neutralized to free the non-salt form.

When following the neutralization desalting is necessary, a common desalting procedure may be employed. For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the addition salt formation either with pharmaceutically acceptable acids (or bases) or non-pharmaceutically acceptable acids (or bases) may be used as a convenient purification technique. After formation and isolation, the addition salt form of GE 81112 compounds can be transformed into the corresponding free-zwitterionic or into a different pharmaceutically acceptable addition salt.

Physico-Chemical Characteristics of GE 81112 Factor A

A) Mass Spectrometry

GE 81112 factor A gives a monoprotonated ion at m/z=644 in MS experiments on a Thermofinnigan LCQ deca instrument fitted with an electrospray source, using Thermofinnigan calibration mix. The electrospray conditions were: Spray Voltage: 4.7 kV; Capillary temperature: 250° C.; Capillary Voltage: 9V; Infusion mode 5 µl/min. Spectra were recorded from a 0.01 mg/ml solution in acetonitrile:water 50:50 (v/v).

FIG. 1 shows a typical MS-MS spectrum of GE 81112 factor A after fragmentation of the monoprotonated ion at m/z=644 with a normalized collisions energy of 25%. GE 81112 factor A gives exact mass of the monoprotonated ion at m/z=644.2186 in experiments on a Bruker Daltonics APEX II, 4.7 Tesla spectrometer fitted with an electrospray source. FTMS conditions were: Electrospray: Analytica Source, off Axis Spray, 60 µl/h; Drying Gas 200° C.; Capillary voltage: 70V; Skimmer Voltage: 10V; Accumulation: 40 Scans; Broad Band Mode Resolution 20'000.

B) Infrared Spectroscopy

The infrared spectrum of GE 81112 factor A is shown in FIG. 2 The spectrum was recorded as nujol mull with an IFS-48 Fourier Transform spectrophotometer.

The following absorption main bands (cm$^{-1}$) were observed: 3356; 2956; 2855; 2256; 2128; 1663; 1596; 1455; 1378; 1345; 1123; 1050; 1026; 1002; 825; 764.

C) $^1$H-NMR and $^{13}$C-NMR

The 600 MHz $^1$H-NMR spectrum (FIG. 3) and the 150 MHz $^{13}$C-NMR spectrum (FIG. 4) of GE 81112 factor A were recorded at 25° C. in DMSO-d$_6$ after addition of trifluoroacetic acid (TFA). In both spectra the signals due to formate, coming from purification process, were detected ($^1$H chemical shift 8.13 and 7.07-7.25 ppm; $^{13}$C chemical shift 163.0 ppm)

Table IV and Table V, report the $^1$H and $^{13}$C NMR signals observed for factor A.

TABLE IV $^1$H-NMR resonances of GE 81112 (factor A) in DMSO-d$_6$ + TFA

| $^1$H Chemical shift (ppm) | Multiplicity |
|---|---|
| 1.52 | br d |
| 1.57-1.67 | m |
| 1.81 | br d |
| 1.88 | m |
| 2.87 | dd |
| 2.90 | m |
| 3.12 | dd |
| 3.15 | m |
| 3.65 | m |
| 3.83 | m |
| 3.94 | br d |
| 4.40 | br s |
| 4.46 | m |
| 4.50 | dd |
| 4.70 | m |
| 5.06 | d |
| 6.46 | br |
| 6.94 | s |
| 7.29 | s |
| 7.99 | d |
| 8.17 | d |
| 8.30 | m |
| 8.57 | br d |
| 8.95 | d |
| 9.06 | br d |
| 14.09 | br |
| 14.27 | br |

TABLE V $^{13}$C-NMR resonances of GE 81112 factor A in DMSO-d$_6$ + TFA

| $^{13}$C Chemical shift (ppm) | Multiplicity |
|---|---|
| 15.9 | t |
| 27.19 | t |
| 28.41 | t |
| 35.31 | t |
| 42.86 | t |
| 50.13 | d |
| 51.30 | d |
| 56.86 | d |
| 59.71 | d |
| 64.07 | d |
| 65.11 | d |
| 66.88 | d |
| 67.76 | t |
| 116.83 | d |
| 118.49 | d |
| 128.41 | s |
| 129.03 | s |
| 133.65 | d |
| 139.66 | s |
| 156.73 | s |
| 167.39 | s |
| 170.16 | s |
| 171.29 | s |
| 171.65 | s |

Physico-Chemical Characteristics of GE 81112 Factor B

A) Mass Spectrometry

GE 81112 factor B gives a monoprotonated ion at m/z=659 in MS experiments on a Thermofinnigan LCQ deca instrument fitted with an electrospray source, using Thermofinnigan calibration mix. The Electrospray conditions were: Spray Voltage: 4.7 kV; Capillary temperature: 250° C.; Capillary Voltage: 9V; Infusion mode 5 µl/min. Spectra were recorded from a 0.01 mg/ml solution in acetonitrile:water 50:50 (v/v).

FIG. 5 shows a typical MS-MS spectrum of GE 81112 factor B after fragmentation of the monoprotonated ion at m/z=659 with a normalized collisions energy of 28%. GE 81112 factor B gives exact mass of the monoprotonated ion at m/z=659.2295 in experiments on a Bruker Daltonics APEX II, 4.7 Tesla spectrometer fitted with an electrospray source. FTMS conditions were: Electrospray: Analytica Source, off Axis Spray, 60 µl/h; Drying Gas 200° C.; Capillary voltage: 70 V; Skimmer Voltage: 10 V; Accumulation: 40 Scans; Broad Band Mode Resolution 20'000.

B) Infrared Spectroscopy

The infrared spectrum of GE 81112 factor B is shown in FIG. 6 The spectrum was recorded in KBr with an IFS-48 Fourier Transform spectrophotometer.

The following absorption main bands (cm$^{-1}$) were observed: 3359; 2958; 2852; 2258; 2129; 1681; 1591: 1450; 1385; 1347; 1122; 1072; 1025; 998; 765.

C) $^1$H-NMR and $^{13}$C-NMR

The 600 MHz $^1$H-NMR spectrum (FIG. 7) and the 150 MHz $^{13}$C-NMR spectrum FIG. 8 of GE 81112 factor B were recorded at 25° C. in DMSO-$d_6$ after addition of trifluoroacetic acid (TFA). In both spectra the signals due to formate, coming from purification process, were detected ($^1$H chemical shift 8.13 and 7.07-7.25 ppm; $^{13}$C chemical shift 163.0 ppm).

Table VI and Table VII report the $^1$H and $^{13}$C NMR signals observed for factor B.

TABLE VI $^1$H-NMR resonances of GE 81112 factor B in DMSO-$d_6$ + TFA

| $^1$H Chemical shift (ppm) | Multiplicity |
|---|---|
| 1.52 | br d |
| 1.57-1.72 | m |
| 1.83 | br d |
| 1.90 | m |
| 2.63 | dd |
| 2.88 | dd |
| 2.92 | m |
| 3.13 | br d |
| 3.64 | m |
| 3.83 | m |
| 3.95 | br d |
| 4.35 | br s |
| 4.46 | m |
| 4.50 | dd |
| 4.60 | m |
| 5.05 | d |
| 6.46 | br |
| 6.48 | s |
| 6.93 | s |
| 7.40 | br s |
| 7.84 | d |
| 8.05 | d |
| 8.33 | m |
| 8.54 | d |
| 9.00 | br d |
| 11.72 | br s |
| 11.75 | br s |
| — | — |

TABLE VII $^{13}$C-NMR resonances of GE 81112 factor B in DMSO-$d_6$ + TFA

| $^{13}$C Chemical shift (ppm) | Multiplicity |
|---|---|
| 15.9 | t |
| 27.36 | t |
| 28.40 | t |
| 35.47 | t |
| 42.87 | t |
| 50.1 | d |

TABLE VII-continued $^{13}$C-NMR resonances of GE 81112 factor B in DMSO-$d_6$ + TFA

| $^{13}$C Chemical shift (ppm) | Multiplicity |
|---|---|
| 51.20 | d |
| 56.78 | d |
| 59.73 | d |
| 64.09 | d |
| 65.14 | d |
| 66.90 | d |
| 67.77 | t |
| 110.3 | d |
| 117.85 | d |
| 122.5 | s |
| 128.4 | s |
| 139.66 | s |
| 146.7 | s |
| 156.7 | s |
| 167.4 | s |
| 170.5 | s |
| 171.3 | s |
| 171.38 | s |

Physico-Chemical Characteristics of GE 81112 Factor B1

A) Mass spectrometry

GE 81112 factor B1 gives a monoprotonated ion at m/z=658 in MS experiments on a Thermofinnigan LCQ deca instrument fitted with an electrospray source, using Thermofinnigan calibration mix. The Electrospray conditions were: Spray Voltage: 4.7 kV; Capillary temperature: 250° C.; Capillary Voltage: 9V; Infusion mode 5 µl/min. Spectra were recorded from a 0.0 mg/ml solution in acetonitrile:water 50:50 (v/v).

FIG. 9 shows a typical MS-MS spectrum of GE 81112 factor B1 after fragmentation of the monoprotonated ion at m/z=658 with a normalized collisions energy of 25%.

GE 81112 factor B1 gives exact mass of the monoprotonated ion at m/z=658.2459 in experiments on a Bruker Daltonics APEX II, 4.7 Tesla spectrometer fitted with an electrospray source. FTMS conditions were: Electrospray: Analytica Source, off Axis Spray, 60 µl/h; Drying Gas 200° C.; Capillary voltage: 70 V; Skimmer Voltage: 10 V; Accumulation: 40 Scans; Broad Band Mode Resolution 20'000

B) $^1$H-NMR and $^{13}$C-NMR

The 600 MHz $^1$H-NMR spectrum (FIG. 10) and the 150 MHz $^{13}$C-NMR spectrum (FIG. 11) of GE 81112 factor B1 were recorded at 25° C. in DMSO-$d_6$. In both spectra the signals due to formate, coming from purification process, were detected ($^1$H chemical shift 8.32 ppm; $^{13}$C chemical shift 165.28 ppm).

Table VIII and Table IX report the $^1$H and $^{13}$C NMR signals observed for factor B1.

TABLE VIII $^1$H-NMR resonances of GE 81112 Factor B1 in DMSO-$d_6$

| $^1$H Chemical shift (ppm) | Multiplicity |
|---|---|
| 1.38 | br d |
| 1.56-1.64 | m |
| 1.76 | m |
| 2.70 | m |
| 2.82 | br s |
| 2.92 | m |
| 3.01-3.06 | m |
| 3.49 | br m |
| 3.57 | br s |
| 4.20 | br dd |
| 4.26 | br |
| 4..40 | br m |

TABLE VIII-continued $^1$H-NMR resonances of GE 81112 Factor B1 in DMSO-d$_6$

| $^1$H Chemical shift (ppm) | Multiplicity |
|---|---|
| 4.46 | m |
| 5.05 | d |
| 5.60 | br s |
| 6.21 | br |
| 6.52 | br |
| 6.78 | br s |
| 7.13 | br |
| 7.80 | br d |
| 7.90 | br d |
| 8.44 | br |

TABLE IX $^{13}$C-NMR resonances of GE 81112 factor B1 in DMSO-d$_6$

| $^{13}$C Chemical shift (ppm) | Multiplicity |
|---|---|
| 17.95 | t |
| 27.97 | t |
| 29.8 | t |
| 36.54 | t |
| 43.75 | t |
| 45.65 | d |
| 50.52 | d |
| 51.9 | d |
| 57.75 | d |
| 61.0 | d |
| 64.03 | d |
| 66.7 | d |
| 66.88 | d |
| 111.07 | d |
| 118.97 | d |
| 122.47 | s |
| 127.88 | s |
| 148.08 | s |
| 159.18 | s |
| 169.44 | s |
| 171.53 | s |
| 171.81 | s |
| 173.08 | s |

Biological Activity

Antimicrobial activity of GE 81112 factors A, B and B1 was determined by using microdilution method with standard U-bottom 96-well plates according to The National Committee for Clinical Laboratory Standards (Methods for Dilution Antimicrobial Susceptibility Tests for Bacteria that Grow Aerobically—Third Edition; Approved Standard. NCCLS document M7-A3 Vol. 13 No. 25). The results are reported in Table 10.

The strains used were clinical isolates or from American Type Culture Collection (ATCC). GE 81112 factors were dissolved in DMSO; this solution was further diluted with distilled water.

The media used were cation-adjusted Mueller Hinton broth (CAMHB) for *Escherichia coli, Staphylococcus aureus, Moraxella catarrhalis, Enterococcus faecalis*; Todd Hewitt broth (THB) for *Streptococcus pyogenes, Streptococcus pneumoniae*; Antibiotic medium No 3 (AM3) and Base Medium Davis Mingioli Broth+2% (w/v) glucose+100 μg/ml asparagine (MM), *Bacillus subtilis*; Davis Mingioli Broth+2% (w/v) glucose (MM) for *Escherichia coli*; RPMI 1640 (RPMI) and Minimal 40+0.1% vitamins (MM) for *Candida albicans*. Unless otherwise indicated inocula were 10$^4$ CFU/ml. All strains were incubated at 35° C. in air. Incubation time was 18-24 hours. Visual readings were performed after incubation and the MIC was defined as the lower concentration that completely inhibited growth of tested microorganisms.

TABLE X

Antimicrobial activity of GE 81112 factors A, B and B1 MIC (μg/ml)

| Strain (Medium) | 81112 A | 81112 B | 81112 B1 |
|---|---|---|---|
| 819 *Staphylococcus aureus* Smith ATCC19636 (CAMHB) | >512 | >512 | >512 |
| 49 *Streptococcus pyogenes* cl. is. (THB) | >512 | 512 | 512 |
| 44 *Streptococcus pneumoniae* cl. is. (THB) | 64 | 64 | 64 |
| 560 *Enterococcus faecalis* Van A (CAMHB) | 32 | 32 | 512 |
| 102 *Bacillus subtilis* ATCC6633 (MM) | 0.13 | 0.008 | 0.06 |
| 102 *Bacillus subtilis* ATCC6633 (AM3) | >512 | 256 | 512 |
| 3292 *Moraxella catarrhalis* cl. is. (CAMHB) | 2 | 1 | 2 |
| 47 *Escherichia coli* (MM) | 0.06 | 0.03 | 0.13 |
| 47 *Escherichia coli* (CAMHB) | >512 | 512 | 512 |
| 145 *Candida albicans* (MM) | >512 | >512 | >512 |
| 145 *Candida albicans* (RPMI) | >512 | >512 | >512 |

GE 81112 factors A, B and B1 inhibit the growth of *Moraxella catarrhalis*, with MIC in the 1-2 μg/ml range. The used strain is a clinical-isolate.

GE 81112 factors A, B and B1 show also marginal activity (MIC 64 μg/ml) against *Streptococcus pneumoniae*, clinical isolate. Moreover, factors A and B have a MIC of 32 μg/ml against *Enterococcus faecalis* resistant to Vancomycin (VanA) whereas factor B1 is not active till concentration of 512 μg/ml.

*M. catarrhalis* and *S. pneumoniae* are recognized important pathogens of humans. They are a common cause of respiratory tract infections, particularly otitis media in children and lower respiratory tract infections in the eldery. *M. catarrhalis* and *S. pneumoniae* have been recently accepted as the commonest pathogens of the respiratory tract (M. C. Enright and H. McKenzy, *Moraxella (Branhamella) catarrhalis*—Clinical and molecular aspect of a rediscovered pathogen, J. Med. Microbiol. 46, 360-71, 1997).

Vancomycin resistant *Enterococci* (VRE) are emerging as important hospital-acquired pathogens responsible for severe human infections (such as endocarditis, meningitis and septicemia) posing an increasing therapeutic challenge (Y. Cetinkaya, P. Falk, C. G. Mayhall, Vancomycin-resistant enterococci, Clin. Microbiol. Rev. 13, 686-707, 2000; L. B. Rice Emergence of vancomycin-resistant enterococci, Emerg. Infec. Dis. 7, 183-7, 2001)

GE 81112 factors A, B and B1 inhibit also at very low concentrations, definitively minor of 1 μg/ml, the growth of *E. coli* and *B. subtilis* when these bacteria are cultivated in minimal media (MM). MICs of factors are A, B and B1 are in the range of 256-512 μg/ml or higher when the same bacteria are grown in rich media.

GE 81112 factors A, B and B1 did not inhibit growth of *Candida albicans* either in minimal medium or in rich medium.

The differential behaviour of GE 81112 factors A, B and B1 to bacteria such as *E. coli* and *B. subtilis* versus an eucaryotic organism such as *C. albicans* suggests that the mechanism of action of GE 81112 compounds is specific for prokaryotic organisms.

According to recent trends in antimicrobial therapy replacing agents with broad spectrum activity with a agents with a more narrow antimicrobial spectrum which (is) are selectively active against the isolated pathogen(s) is favoured because it reduces the selective pressure to develop resistance (J. C. Gyssens: "Quality Measures of Antimicrobial Drug Use" in Int. J. Antimicrobial Agents, 17, 2001, 9-19; J. Chopra "Research and Development of Antibacterial Agents" in Current Opinion in Microbiology, 1998, 1, 495-501). Therefore, the GE 81112 compounds of this invention are particularly suitable for use as selective agents for treatment of respiratory tract infections due to *M. catarrhalis*.

The compounds of the invention can be administered, as a pharmaceutically acceptable composition, as such or in admixture with a pharmaceutically acceptable carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

The compounds of the invention can be accordingly used as a medicament; the single factors A, B and B1 can be utilized alone or as a mixture of two or more of them, in any proportion. Said mixture may be obtained by mixing predetermined amounts of two or more factors. Alternatively, mixtures of the factors can be directly obtained from the isolation of the fermentation product of *Streptomyces* sp. DSMZ 14386 according to the above described process.

Preferably, the compounds of the invention, are formulated into formulations suitable for parenteral and/or oral and/or topical administration, according to procedures known per se in the art and reported in reference books.

For i.v. administration in the treatment of any infection involving a microorganism susceptible to the antibiotic, a pharmaceutical formulation is, for instance, in water with an appropriate solubilising agent such as polypropylene glycol or dimethylacetamide and a surface-active agent such as polyoxyethylene sorbitan mono-oleate or polyethoxylated castor oil in sterile water for injection. Preferably, a formulation for injection should have a pH in the range of 7±0.5. If necessary, it might be advisable to adjust the pH of the preparation with a suitable buffering agent. Conveniently, phosphate can be used as buffering agent.

Alternatively, the active ingredient may be prepared as a lyophilized powder for reconstitution. Optionally, a common lyophilization aid can be added, if necessary, to obtain a lyophilized material in powder form.

The antibiotic may also be used in a suitable pharmaceutical form such as a capsule, a tablet or an aqueous solution or suspension (e.g. syrups) for oral administration or incorporated into conventional creams or jellies for topical applications or in liquid formulations suitable for inhalation therapy.

The dosage of the active ingredient depends on many factors which include type, age and conditions of the patient, specific active ingredient and formulation selected for the administration, administration schedule, etc. In general, effective antimicrobial dosages are employed per single unit dosage form. Repeated applications/administrations, e.g. from 2 to 6 times a day, are in general preferred. An effective dosage may be in general in the range 0.5-50 mg/kg body weight/day. A preferred topic preparation is an ointment containing from 1% to 10% of a compound of the present invention.

Anyway, the prescribing physician will be able to determine the optimal dosage for a given patient in a given situation.

BRIEF DESCRIPTION OF THE DRAWINGS

FIG. 1 represents MSMS spectra of antibiotic GE 81112 factor A after fragmentation of the monoprotonated ion at m/z=644 with a normalized collisions energy of 25%.

FIG. 2 represents the I.R. absorption spectrum of antibiotic GE 81112 factor A in nujol mull.

FIG. 3 represents the $^1$H-NMR spectrum of antibiotic GE 81112 factor A, measured at 600 MHz in DMSO-$d_6$ and TFA (drops).

FIG. 4 represents the proton decoupled $^{13}$C-NMR spectrum of antibiotic GE 81112 factor A at 150 MHz in DMSO-$d_6$ and TFA (drops).

FIG. 5 represents MsMs spectrum of antibiotic GE 81112 factor B after fragmentation of the monoprotonated ion at m/z=659 with a normalized collisions energy of 28%.

FIG. 6 represents the I.R. absorption spectrum of antibiotic GE 81112 factor B in KBr.

FIG. 7 represents the $^1$H-NMR spectrum of antibiotic GE 81112 factor B, measured at 600 MHz in DMSO-$d_6$ and TFA (drops).

FIG. 8 represents the proton decoupled $^{13}$C-NMR spectrum of antibiotic GE 81112 factor B at 150 MHz in DMSO-$d_6$ and TFA (drops).

FIG. 9 represents MsMs spectrum of antibiotic GE 81112 factor B1, after fragmentation of the monoprotonated ion at m/z=658 with a normalized collisions energy of 25%.

FIG. 10 represents the $^1$H-NMR spectrum of antibiotic GE 81112 factor B1, measured at 600 MHz in DMSO-$d_6$.

FIG. 11 represents the proton decoupled $^{13}$C-NMR spectrum of antibiotic GE 81112 factor B1 at 150 MHz in DMSO-$d_6$.

The following examples further illustrate the invention without limiting it.

EXAMPLE 1

Fermentation of *Streptomyces* sp. DSMZ 14386 and recovery of GE 81112 compounds from the harvested broth.

The seed culture, stored at −80° C. in vials, was used to inoculate a 500 ml Erlenmeyer flask containing 100 ml of V6 medium (V6) having the following composition (g/l): glucose 20, meat extract 5, yeast extract 5, peptone 5, hydrolized casein 3 and NaCl 1.5. The medium was prepared with distilled water and the pH was adjusted to 7.5 with NaOH before sterilization at 120° C. for 20 min. The inoculated flask was incubated for 40-48 hours at 28° C. on a rotatory shaker at 200 rpm and then was used to inoculate a 4 liter bioreactor containing 3 liter of V6 medium. The culture was grown at a temperature of 27° C. for the first 30 hours and then at 24° C. for the following 18 hours till the inoculation time. Stirring was kept at 700 rpm, with an air flow of 0.5 v/v/min. This culture (1.5 liter) was inoculated into a 300 liter fermenter containing 200 liter of production medium having the following composition (g/l): glycerol 30, soybean meal 15, calcium carbonate 5 and sodium chloride 2. The medium was prepared with deionized water and the pH was adjusted to 7.3 with NaOH. 30 ml of Hodag AFM-5 were added as antifoaming agent. This culture was fermented for 62 hours at 28° C., with an air flow of 60 l/min for the first 18 hours and then increased to 100 l/min (0.5 v/v/min) till the harvest time. The agitation was a 180 rpm.

The harvested broth was then diluted to 200 l with distilled water and was filtered after addition of Hyflo filter aid. The mycelium was discharged and the filtrate was brought to pH 3.5 by addition of about 600 ml of 3.25 M HCl. The GE 81112 antibiotic mixture was then adsorbed on 2.5 l of Dowex 50W×2 cation exchange resin in the acid form (The Dow Chemical Company) After stirring batchwise overnight the resin was recovered by filtration and the broth was discharged. Two fermenters were processed in parallel as above described and the Dowex resins from the individual runs were then pooled. The resin (5 l) was loaded on a column (12.5 cm diameter; 45 cm bed height), and was washed at 90 ml/min flow rate with 6 l of 20 mM sodium phosphate pH 3.5 buffer; then with 10 l of 20 mM sodium phosphate pH 3.5 buffer: methanol 8:2 (v/v) mixture. Elution was then performed with 257 mM ammonia buffered to pH 10 with phosphoric acid. One-liter fractions were collected which were immediately brought to about pH 6 by addition of phosphoric acid. The content in antibiotic of each fraction was evaluated by bioassay i.e inhibition of the growth of E. coli and B. subtilis cultivated in Minimal Medium (MM) and by analytical HPLC, according to the method described in Example 2. Fractions 5-10 eluted from the Dowex resin were pooled yielding 5.8 l of solution enriched in the GE 81112 compounds mixture. A sample (50 ml) of this solution was concentrated under vacuum and was then lyophilized yielding 1.48 gr of crude GE 81112 compounds preparation.

EXAMPLE 2

Isolation and Purification of GE 81112 Factors A, B1 and B

The solution obtained as in Example 1 was stirred overnight batch-wise with 1.2 l of polystyrenic resin HP20 (MitsubishI Chemicals Co.). The resin was then recovered by filtration and was loaded on 7.5 cm diameter per 27 cm bed height column. The column was then eluted at 40 ml/min flow rate with 6 l of 1:9 (v/v) methanol: distilled water and then with 4 l of a 3:7 (v/v) mixture. One-liter fractions were collected and analyzed by HPLC. The first three fractions contained a mixture of GE 81112 factors enriched in factor A and were pooled. The following three fractions were enriched in factors B1 and B and were also pooled. The two pools were concentrated under vacuum to a small volume and were then lyophilized, yielding 3.8 gr and 1.7 gr of solids enriched in factor A and in factors α1 plus B, respectively.

The individual pure factors were then obtained by preparative HPLC (Shimadzu-LC8A) on a Hibar Lichrosorb (Merck) 25×250 mm column RP8 (7 μm particle size) which was eluted at 3.5 ml/min flow rate with 40 mM ammonium formate brought to pH 4.5 with formic acid. About 100 mg of the above antibiotic preparations were dissolved in 350 μm of eluting phase and were processed per chromatographic run. Factor A, B1 and B were typically eluted after about 9.5, 12.4 and 13.4 min, respectively. The fractions of repeated chromatographic runs which showed homogeneous antibiotic content were pooled and were concentrated under vacuum to water residue. The solutions were then lyophilized, dissolved again in 40 ml of distilled water and re-lyophilized to yield 116, 13, 10 mg of antibiotic GE 81112 factor A, B1 and B, respectively.

HPLC analysis was performed on a Shimadzu LC10-AS instrument, equipped with SPD-M10A diode array detector and Sil-9A autoinjector. The chromatographyc column was an "Altima" RP18, 5 μm, 250×4.6 mm i.d, purchased from Alltech. Isocratic elution was performed at 1 ml/min flow rate, with 40 mM ammonium formate buffer brought to pH 4.5 by addition of formic acid. UV detection was at 230 nm.

The three factors were tested under the analytical HPLC conditions described above and showed the following retention times: factor A, 14.1 min., factor B1, 18.4 min. and factor B 21.6 min.

The invention claimed is:
1. Isolated antibiotic GE 81112 Factor B having the following characteristics:
   A) Mass spectrum recorded from a 0.01 mg/ml solution in acetonitrile:water 50:50 giving a monoprotonated ion at 659 m/z on a Thermofinnigan LCQ deca instrument under the following electrospray conditions: Spray Voltage: 4.7 kv; Capillary temperature: 250° C.; Capillary Voltage: 9V; Infusion mode 5 μl/min.
   B) Infrared spectrum (FIG. 6) recorded in KBr with an IFS-48 Fourier Transform spectrophotometer showing the following main bands ($cm^{-1}$):
   3359; 2958; 2852; 2258; 2129; 1681; 1591; 1450; 1385; 1347; 1122; 1072; 1025; 998; 765
   C) $^1$H-NMR spectrum (FIG. 7) recorded at 600 MHz at 25° C. in DMSO-$d_6$ and trifluoroacetic acid (drops) showing the following $^1$H signals:

| Chemical shift (ppm) | Multiplicity |
| --- | --- |
| 1.52 | br d |
| 1.57-1.72 | m |
| 1.83 | br d |
| 1.90 | m |
| 2.63 | dd |
| 2.88 | dd |
| 2.92 | m |
| 3.13 | br d |
| 3.64 | m |
| 3.83 | m |
| 3.95 | br d |
| 4.35 | br s |
| 4.46 | m |
| 4.50 | dd |
| 4.60 | m |
| 5.05 | d |
| 6.46 | br |
| 6.48 | s |
| 6.93 | s |
| 7.40 | br s |
| 7.84 | d |
| 8.05 | d |
| 8.33 | m |
| 8.54 | d |
| 9.00 | br d |
| 11.72 | br s |
| 11.75 | br s |
| — | — |

D) $^{13}$C-NMR spectrum (FIG. 8) recorded at 150 MHz, at 25° C. in DMSO-$d_6$ and trifluoroacetic acid (drops) showing the following $^{13}$C signals

| $^{13}$C Chemical shift (ppm) | Multiplicity |
| --- | --- |
| 15.9 | t |
| 27.36 | t |
| 28.40 | t |
| 35.47 | t |
| 42.87 | t |
| 50.1 | d |
| 51.20 | d |
| 56.78 | d |
| 59.73 | d |
| 64.09 | d |
| 65.14 | d |

-continued

| ¹³C Chemical shift (ppm) | Multiplicity |
|---|---|
| 66.90 | d |
| 67.77 | t |
| 110.3 | d |
| 117.85 | d |
| 122.5 | s |
| 128.4 | s |
| 139.66 | s |
| 146.7 | s |
| 156.7 | s |
| 167.4 | s |
| 170.5 | s |
| 171.3 | s |
| 171.38 | s |

E) Retention time 21.6 min, determined by using an analytical HPLC Shimadzu LC10-AS, equipped with an "Altima" RP18, 5 μm, 250×4.6 mm i.d column; isocratic elution performed at 1 ml/min. flow rate, with 40 mM ammonium formate buffer, brought to pH 4.5 by addition of formic acid; UV detection at 230 nm.

2. Isolated antibiotic GE 81112 factor B1 having the following characteristics:

A) Mass spectrum recorded from a 0.01 mg/ml solution in acetonitrile:water 50:50 giving a monoprotonated ion at 658 m/z ib a Termofinnigan LCQ deca instrument under the following electrospray conditions; Spray Voltage: 47 kv; Capillary Temperature: 250° C.; Capillary voltage: 9V; Infusion Mode: 5 1/min.

B) H-NMR spectrum (FIG. 10) recorded at 600 MH at 25° C. in DMSO-$d_6$ showing the following ¹H signals:

| Chemical shift (ppm) | Multiplicity |
|---|---|
| 1.38 | br d |
| 1.56-1.64 | m |
| 1.76 | m |
| 2.70 | m |
| 2.82 | br s |
| 2.92 | m |
| 3.01-3.06 | m |
| 3.49 | br m |
| 3.57 | br s |
| 4.20 | br dd |
| 4.26 | br |
| 4.40 | br m |
| 4.46 | m |
| 5.05 | d |
| 5.60 | br s |
| 6.21 | br |
| 6.52 | br |
| 6.78 | br s |
| 7.13 | br |
| 7.80 | br d |
| 7.90 | br d |
| 8.44 | br |

C) ¹³C-NMR spectrum (FIG. 11) recorded at 150 Mhz, at 25° C. in DMSO-$d_6$ showing the following ¹³C signals:

| Chemical shift (ppm) | Multiplicity |
|---|---|
| 17.95 | t |
| 27.97 | t |
| 29.8 | t |
| 36.54 | t |
| 43.75 | t |
| 45.65 | d |
| 50.52 | d |
| 51.9 | d |
| 57.75 | d |
| 61.0 | d |
| 64.03 | d |
| 66.7 | d |
| 66.88 | d |
| 111.07 | d |
| 118.97 | d |
| 122.47 | s |
| 127.88 | s |
| 148.08 | s |
| 159.18 | s |
| 169.44 | s |
| 171.53 | s |
| 171.81 | s |
| 173.08 | s |

D) Retention time 18.4 min, determined by using an analytical HPLC Shimadzu LC10-AS, equipped with an "Altima" RP18, 5 μm, 250×4.6 mm i.d column; isocratic elution performed at 1 ml/min. flow rate, with 40 mM ammonium formate buffer brought to pH 4.5 by addition of formic acid; UV detection at 230 nm.

\* \* \* \* \*